(12) United States Patent
Butterfield et al.

(10) Patent No.: US 6,290,650 B1
(45) Date of Patent: *Sep. 18, 2001

(54) TONOMETRY SYSTEM FOR MONITORING BLOOD PRESSURE

(75) Inventors: Robert D. Butterfield, Poway; Kenneth J. Pytel; Charles R. Holdaway, both of San Diego; Stephen A. Martin, Carlsbad, all of CA (US)

(73) Assignee: Alaris Medical Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/321,907

(22) Filed: May 28, 1999

Related U.S. Application Data

(63) Continuation of application No. 08/848,920, filed on May 1, 1997, now Pat. No. 5,908,027, which is a continuation of application No. 08/642,081, filed on May 1, 1996, now abandoned, which is a continuation of application No. 08/284,326, filed on Aug. 2, 1994, now abandoned.

(51) Int. Cl.[7] ............................................. A61B 5/02
(52) U.S. Cl. ................................. 600/485; 600/503
(58) Field of Search ................... 600/485, 490, 600/491, 500–503

(56) References Cited

U.S. PATENT DOCUMENTS

| | | | |
|---|---|---|---|
| 2,660,164 | 11/1953 | Hasbrouck, Jr. | 128/2.05 |
| 3,090,377 | 5/1963 | Salisbury et al. | 128/2.05 |
| 3,099,262 | 7/1963 | Bigliano | 128/2.05 |
| 3,219,035 | 11/1965 | Pressman et al. | 128/2.05 |
| 3,517,999 | 6/1970 | Weaver | 356/32 |
| 3,527,204 | 9/1970 | Lem et al. | 128/2.05 |
| 3,572,320 | 3/1971 | Gerold et al. | 128/2.05 |
| 3,782,368 | 1/1974 | Reibold | 128/2.08 |
| 3,842,357 | 10/1974 | Hutchins | 328/188 |
| 3,935,984 | 2/1976 | Lichowsky et al. | 128/2.05 C |
| 3,991,746 | 11/1976 | Hanna | 128/2 S |
| 4,085,740 | 4/1978 | Allen, Jr. | 128/2.05 R |
| 4,185,641 | 1/1980 | Minior et al. | 128/675 |
| 4,202,347 | 5/1980 | Sacks | 128/677 |
| 4,211,289 | 7/1980 | Klein | 172/686 |
| 4,269,193 | 5/1981 | Eckerle | 128/672 |
| 4,307,728 | 12/1981 | Walton | 128/687 |
| 4,406,289 | 9/1983 | Wesseling et al. | 128/670 |
| 4,423,738 | 1/1984 | Newgard | 128/672 |
| 4,429,700 | 2/1984 | Thees et al. | 128/681 |
| 4,441,504 | 4/1984 | Peterson et al. | 128/686 |
| 4,572,204 | 2/1986 | Stephens | 128/675 |
| 4,658,829 | 4/1987 | Wallace | 128/672 |
| 4,712,566 | 12/1987 | Hok | 128/748 |
| 4,718,428 | 1/1988 | Russell | 128/679 |
| 4,727,730 | 3/1988 | Boiarski et al. | 128/667 |
| 4,799,491 | 1/1989 | Eckerle | 128/672 |
| 4,802,488 | 2/1989 | Eckerle | 128/672 |
| 4,803,992 | 2/1989 | Lemelson | 128/634 |
| 4,836,213 | 6/1989 | Wenzel et al. | 128/672 |
| 4,860,760 | 8/1989 | Miyawaki et al. | 128/680 |

(List continued on next page.)

*Primary Examiner*—John P. Lacyk
(74) *Attorney, Agent, or Firm*—Fulwider Patton Lee & Utecht, LLP

(57) ABSTRACT

A system for noninvasively continuously monitoring arterial blood pressure includes a tissue stress sensor that has a continuous diaphragm for sensing stress within tissue adjacent a preselected artery caused by arterial pulsations within that artery. The stress sensitive diaphragm is coupled with electromechanical means for producing electrical signals that represent the stress within the tissue that is communicated to the sensor. These signals are then processed electronically in order to yield an output that is indicative of the arterial blood pressure of the preselected artery. The disclosed system includes methods of operation for determining blood pressure while maintaining a preselected artery in an optimum applanation state and an off-optimum applanation state.

10 Claims, 7 Drawing Sheets

U.S. PATENT DOCUMENTS

| | | | |
|---|---|---|---|
| 4,893,631 | 1/1990 | Wenzel et al. | 128/672 |
| 4,901,733 | 2/1990 | Kaida et al. | 128/687 |
| 4,928,701 | 5/1990 | Harada et al. | 128/677 |
| 4,951,679 | 8/1990 | Harada | 128/672 |
| 4,987,900 | 1/1991 | Eckerle et al. | 128/672 |
| 4,993,422 | 2/1991 | Hon et al. | 128/672 |
| 5,119,822 | 6/1992 | Niwa | 128/672 |
| 5,154,680 | 10/1992 | Drzewiecki et al. | 128/672 |
| 5,158,091 | 10/1992 | Butterfield et al. | 128/672 |
| 5,183,050 | 2/1993 | Kawamura | 128/687 |
| 5,195,522 | 3/1993 | Pytel et al. | 128/680 |
| 5,240,007 | 8/1993 | Pytel et al. | 128/672 |
| 5,261,412 | 11/1993 | Butterfield et al. | 128/672 |
| 5,263,484 | 11/1993 | Martin et al. | 128/672 |
| 5,271,405 | 12/1993 | Boyer et al. | 128/672 |
| 5,273,046 | 12/1993 | Butterfield et al. | 128/672 |

TONOMETRY SYSTEM FOR MONITORING BLOOD PRESSURE

RELATED APPLICATIONS

This is a continuation of Ser. No. 08/848,920, filed May 1, 1997, now U.S. Pat. No. 5,908,027 which is a continuation of Ser. No. 08/642,081, filed May 1, 1996, now abandoned which is a continuation of Ser. No. 08/284,326, filed Aug. 2, 1994 now abandoned.

BACKGROUND OF THE INVENTION

1. Field of the Invention

This invention relates generally to a system for monitoring blood pressure, and more specifically, to a combination of devices and a methodology for non-invasively monitoring the blood pressure waveform in a blood vessel by detecting tissue stress in a blood vessel wall and surrounding tissue.

2. Cross-Reference

The following United States patents have common inventorship and common assignee of interest with this application and each of them are hereby incorporated by reference into this specification: U.S. Pat. Nos. 5,158,091; 5,271,405; 5,240,007; 5,195,522; 5,273,046; 5,261,412; and 5,263,584.

3. The Prior Art

Methods for accurately monitoring the blood pressure waveform have been under investigation for some time. While invasive methods can provide accurate waveforms, the trauma caused to a patient makes such techniques undesirable in many cases. One such method involves the use of a fluid filled catheter inserted into a patient's artery. While accurate blood pressure measurements can be obtained by this method, the negative effects on the patient often outweigh the benefits of achieving accurate results from such a method.

Routine methods of monitoring a patient's blood pressure waveform include the widely used ausculatory method known as the Korotkoff method. This method is non-invasive, however, it only provides a measurement of systolic and diastolic pressure on an intermittent basis; it does not provide the entire waveform on a continuous basis. Furthermore, use of the Korotkoff method often yields inaccurate results. Moreover, the rate at which blood pressure can be recorded is limited by the inflation and deflation rate of the occlusive cuff. Therefore, true beat-to-beat continuous blood pressure monitoring is not possible using this method.

While the occlusive cuff instruments have been adequate for ascertaining long term trends in patient blood pressure, short term variation has previously not been easily measured non-invasively. Techniques that offer potential in this area include a method using a pressure-feedback technique that records the blood pressure in a patient's finger. Feedback error signals are obtained using optical plethysmography. Such methods include several draw backs. One is that blood pressure measurement is too peripheral and undesirably influenced by the smooth muscle tone of the artery. Secondly, it is difficult to implement arterial tonometry with previously available devices because a high degree of miniaturization is required for contact stress sensors used in available devices. For example, one type of arterial tonometer includes an array of individual transducer elements placed directly on the patient's tissue overlying an artery or blood vessel from which blood pressure is to be determined. The elements directly sense the mechanical forces in the tissue with which each of them is in contact. The elements of the array are dimensioned and spaced apart from each other such that a plurality of these elements are required to cover the entire diameter or width of the underlying blood vessel; the size of each element is assigned to cover only a small fraction of the diameter of the underlying blood vessel. The pressure of the array against the tissue is increased to properly applanate the underlying vessel without causing occlusion. The fluid pressure within the artery is then conducted through the vessel wall and the overlying tissue to the transducers.

A significant draw back to such devices includes the use of the discrete elements. It is believed that with such tonometers a continuous contour of the tissue stresses under the array is not accurately obtained because the discrete elements inherently confine the system resolution. Additionally, it is believed that in prior methods no compensation means is provided for motion artifacts which may affect the forces translated to the sensors from the artery.

In view of the above, there is a need for true beat-to-beat, continuous arterial blood pressure measurement. Current research indicates that changes in the pulse waveform due to wave reflection can be responsible for an increase in systolic pressure. Monitoring such a pulse waveform can be crucial, for example, during surgical procedures. Cuff-based techniques are used to monitor blood pressure during surgery. However, a cuff-based technique provides limited ability to monitor the pulse waveform on a continuous basis. Similarly, continuous measurement of pressure during exercise has been limited.

Therefore, it is desirable to provide an arterial tonometry system that is designed for noninvasively continuously measuring arterial blood pressure. This invention addresses these needs and provides the additional capability of determining short term or long term blood pressure trends for any particular patient, depending on the needs of a particular situation.

SUMMARY OF THE INVENTION

In its most general terms, this invention provides a system and methodology for noninvasively continuously monitoring a patient's arterial blood pressure. The methodology associated with this invention includes four basic steps and preferably uses a tissue stress sensor that has a continuous diaphragm. The four basic steps associated with this invention are: placing the sensor having the continuous diaphragm against tissue that is adjacent a preselected artery (preferably by using data from the sensor to determine the desire degree of applanation); applanating the preselected artery, using the sensor to bear against the tissue that is adjacent to the preselected artery; determining a monitoring portion on the sensor that is best suited for acquiring blood pressure information given the location of the sensor relative to the preselected artery and the patient's anatomy; and determining a stress that is communicated to the sensor at the monitoring portion that is caused by arterial pulsations. In this general manner, the arterial blood pressure is determined based on the determination of the stress that is communicated to the sensor.

The continuous diaphragm sensor that is used in connection with this invention is capable of providing a continuous reading of the arterial blood pressure over relatively long periods of time. Moreover, the inventive methodology provides the ability to utilize the continuous diaphragm sensor associated with this invention to safely and accurately monitor a patient's arterial blood pressure for any preselected amount of time.

The tonometry system associated with this invention includes, in general terms, a tissue contact stress sensing device that has a continuous wafer diaphragm for placing against a patient's tissue adjacent a preselected artery. The continuous diaphragm is adapted to be deformed in response to stress in the adjacent tissue caused by the arterial blood pressure within the artery. The sensor also has means for producing an electrical signal that corresponds to the stress at the surface of the tissue. The system associated with this invention also includes a means for receiving the electrical signal from the sensor and for processing that signal in a manner that enables a medical professional to interpret a display that yields blood pressure information. The tonometry system of this invention also includes a mounting apparatus for mounting the sensor, just described in general terms, on a preselected point of the patient's anatomy in order to accurately position the sensor adjacent the preselected artery. Also included is means for moving the sensor to bear against the tissue adjacent the preselected artery such that the sensor effectively applanates the preselected artery. The sensor also preferably includes means for determining a monitoring portion on the sensor, wherein the monitoring portion is that portion of the sensor which is located relative to the preselected artery and is best suited for yielding accurate blood pressure monitoring signals.

These and other features and objects of this invention will become apparent to one skilled in the art from the following detailed description and the accompanying drawings illustrating features of this invention by way of example.

DETAILED DESCRIPTION OF THE PREFERRED EMBODIMENTS

Figure 1:
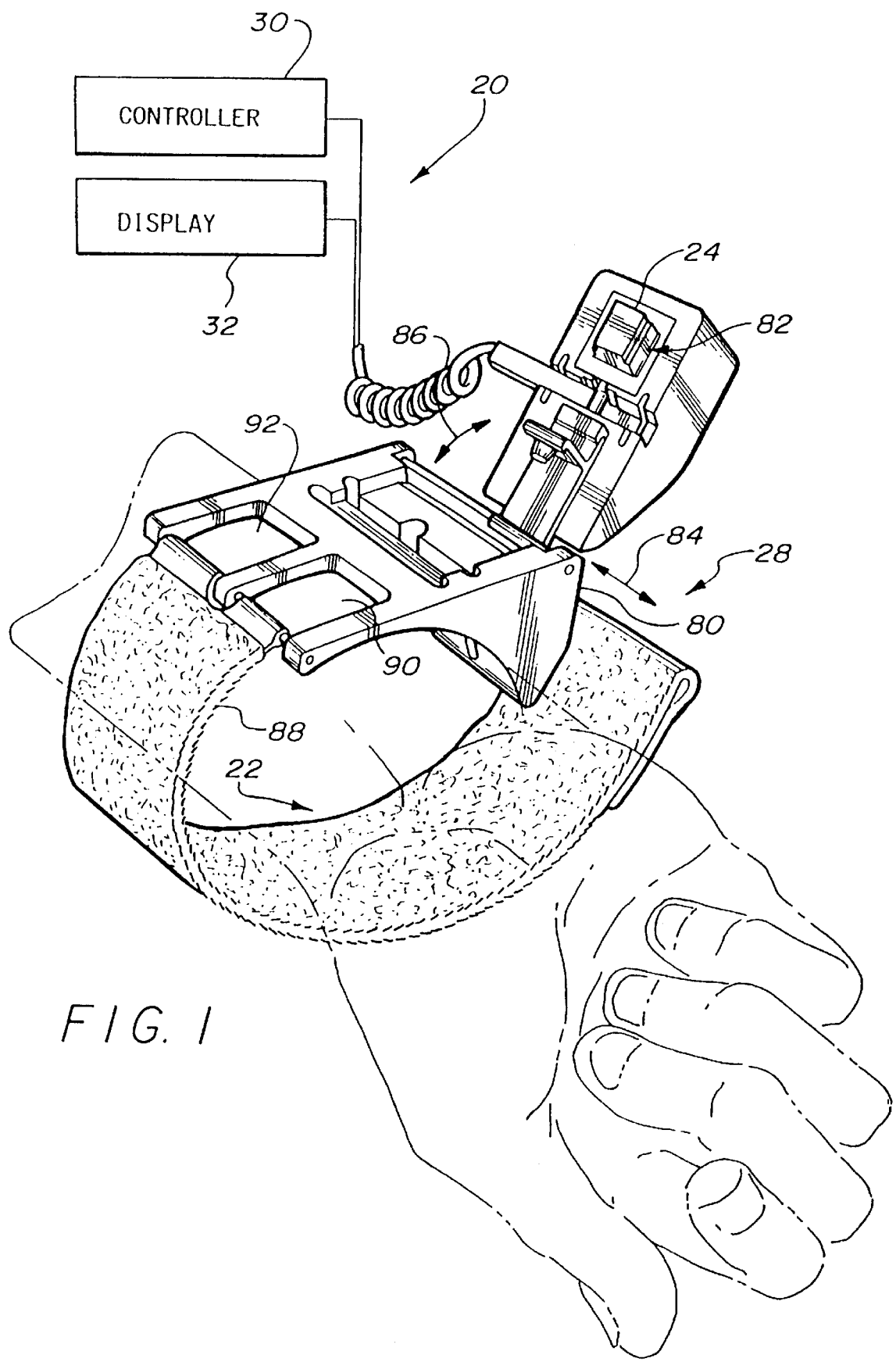
FIG. 1 is a diagrammatic representation of a tonometry system designed in accordance with this invention applied to a patient's wrist.
Figure 2:
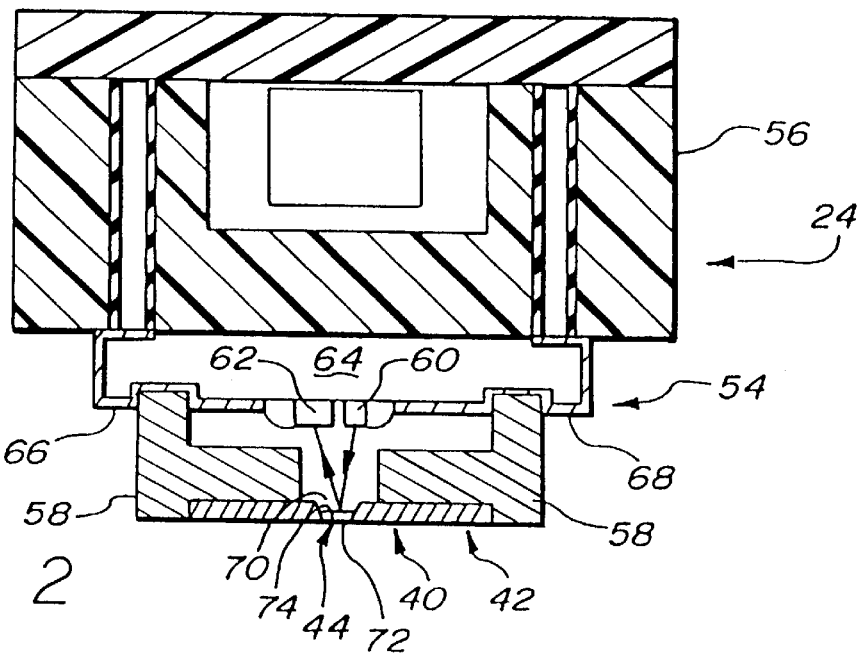
FIG. 2 is a diagrammatic schematic representation of a sensor having a continuous diaphragm used with this invention.

FIG. 1 illustrates, in diagrammatic and block diagram form, tonometry system 20 as applied to a patient's wrist 22 in order to monitor blood pressure within the radial artery of the patient. Sensor 24 is strategically placed within housing 26 such that sensor 24 is capable of communicating with the tissue adjacent the radial artery (or any preselected artery of interest) when mounting apparatus 28 is properly applied to the preselected portion of the patient's anatomy. The interaction between housing 26 and mounting apparatus 28 will be described in further detail below. Tonometry system 20 also includes control electronics 30. Control electronics 30 preferably includes microprocessor means for calculating various variables and parameters associated with continuously monitoring inter-arterial blood pressure. Control electronics 30 also preferably includes means for determining parameters such as an applanation index and means for processing electrical signals from sensor 24 that correspond to a pressure estimation of the arterial blood pressure. Control electronics 30 are coupled with output display device 32 which is also shown coupled to sensor 24. Output display device 32 preferably includes a means for displaying blood pressure determination information, means for indicating the position of the preselected artery relative to sensor 24 and means for aiding a medical professional in positioning sensor 24 relative to the artery of interest in order to obtain the most accurate blood pressure estimation information.

Tonometry system 20 facilitates continuously monitoring the patient's arterial blood pressure non-invasively by sensing the time varying surface tissue contact stresses in regions immediately over and in the vicinity of the preselected artery. In general, the artery to be measured is preferably superficial and overlaying relatively rigid structures. The arteries most commonly used for tonometric blood pressure determination include the radial artery in the wrist, the superficial temporal artery in the forehead and the dorsalis pedis artery in the foot. For purposes of this disclosure, the radial artery in the wrist will be used as the main artery of discussion; however, the tonometry system of this invention is equally applicable to any superficial artery that overlays a relative rigid body structure.

The details of the various elements of tonometry system 20, briefly outlined above, will now be described in order to enable those skilled in the art to practice this invention.

The Sensor

An important element of this invention is sensor 24 and its surrounding structure. Because sensor 24 is used to compress or applanate the radial artery during blood pressure measurement and to measure the contact stress in the tissue adjacent the radial artery, the geometry of sensor 24 and its surrounding structure are vital to the proper conduction of stresses from the radial artery to the tissue surface.

Referring now to FIGS. 2 through 4b, sensor 24 includes wafer 40 which has a nonresponsive portion 42 and a responsive portion (diaphragm) 44. The nonresponsive portion 42 serves mainly to support and press responsive portion 44 upon tissue overlying the radial artery. Under normal conditions when sensor 24 is not being applied to the tissue surrounding the radial artery, the radial artery has a generally rounded cross section. As wafer 40 of sensor 24 is pressed upon the tissue adjacent or overlying the radial artery, the radial artery begins to applanate or flatten along its top surface (where the top of the artery is considered that surface of the artery closest to sensor 24) causing responsive portion 44 of wafer 40 to deflect slightly inward. As the blood pressure within the radial artery changes (i.e., through arterial pulsations), stress is created in tissue 46 which disturbs the equilibrium between responsive portion 44 of wafer 40 and top surface 48 of overlying tissue. This disturbance in equilibrium causes movement between diaphragm 44 and the surface of the tissue. Such movement exists until a new equilibrium is established. The ability of diaphragm 44 to move and assume a unique displacement position for a given blood pressure within radial artery 52 forms the fundamental mechanism whereby sensor 24 is able to transduce the arterial pressure of radial artery 52.

Tissue contact stress sensor 24 includes sensor head 54 and base portion 56. Sensor head 54 comprises the transducer portion of sensor 24. Sensor base portion 56 includes electronic circuitry and other mechanical support structure necessary for properly operating sensor head 54. Sensor head 54 preferably includes six elements: sensor wafer 40, spacing structure 58, infrared emitting diodes (typified at 60), photoreceivers (typified at 62), emitter/detector substrate 64 and circuit traces 66, 68.

An important feature of sensor 24 centers around the material construction of wafer 40. Sensor wafer 40 is preferably formed from a wafer of single crystal silicon (SCS). Responsive diaphragm portion 44 of wafer 40 is preferably formed by chemical microetching a trough 70 in the face of SCS wafer 40. This trough has a tetragonal pyramidal geometry due to the crystal structure of the SCS wafer 40. The body of the trough area 72 defines responsive diaphragm portion 44 of wafer 40. This portion defines a thin diaphragm region of highly controlled thickness and geometry. A major advantage in using SCS in constructing diaphragm 44 is its superior engineering properties and its ability to be micro-machined which in turn provides a one-piece structure essentially free of pre-stressing. Additional benefits in using SCS material include its ability to replicate small geometric features precisely and repeatedly, its linear elastic properties (i.e., almost no hysteresis) and its ability to quickly evidence its failed condition (under failure, the SCS diaphragm 44 totally fails thereby immediately evidencing its failed condition). This is to be contrasted with other materials which, under failure, do not fracture as does SCS, but rather undergo inelastic deformation. Once a diaphragm not made of SCS undergoes any inelastic deformation, it loses its calibration but generally does not manifest its extreme, failed condition, thereby usually going unnoticed and providing inaccurate results in blood pressure measurement.

Underside 74 of trough 70 is preferably metalized with a reflective material such as aluminum or gold. The thickness of the aluminum or gold is preferably approximately 600 angstroms and its purpose will be explained briefly below. Responsive portion 44 of wafer 40 changes its geometry with applied stress as a function of the material properties of the diaphragm. It is important to note that a coating of aluminum or gold 600 angstroms in thickness does not materially alter the properties of diaphragm portion 44 of wafer 40. In the construction of tonometry sensors, the elasticity of responsive portion 44 of wafer 40 must be compatible with the characteristics of human tissue. If diaphragm surface 40 deforms excessively when responding to the stress of surface tissue 46, the tissue surface stress contour transduced by the sensor will be distorted, potentially affecting the accuracy of the measurement. Calculations, numerical simulation and experimental data have shown that diaphragm 44 of wafer 40 should be generally 50 times stiffer than that typical of tissue overlying the artery of interest. The strain rate of the preferred embodiment is 0.24 micro-inch/mmHg measured at the midline of responsive diaphragm portion 44 of wafer 40.

Further details of the construction and function of sensor 24 are explained in U.S. Pat. No. 5,158,091, issued on Oct. 27, 1992, and having common inventorship and Assignee of interest with this application. The teachings of U.S. Pat. No. 5,158,091 are hereby incorporated by reference into this specification.

The Mounting Apparatus

Figure 3:
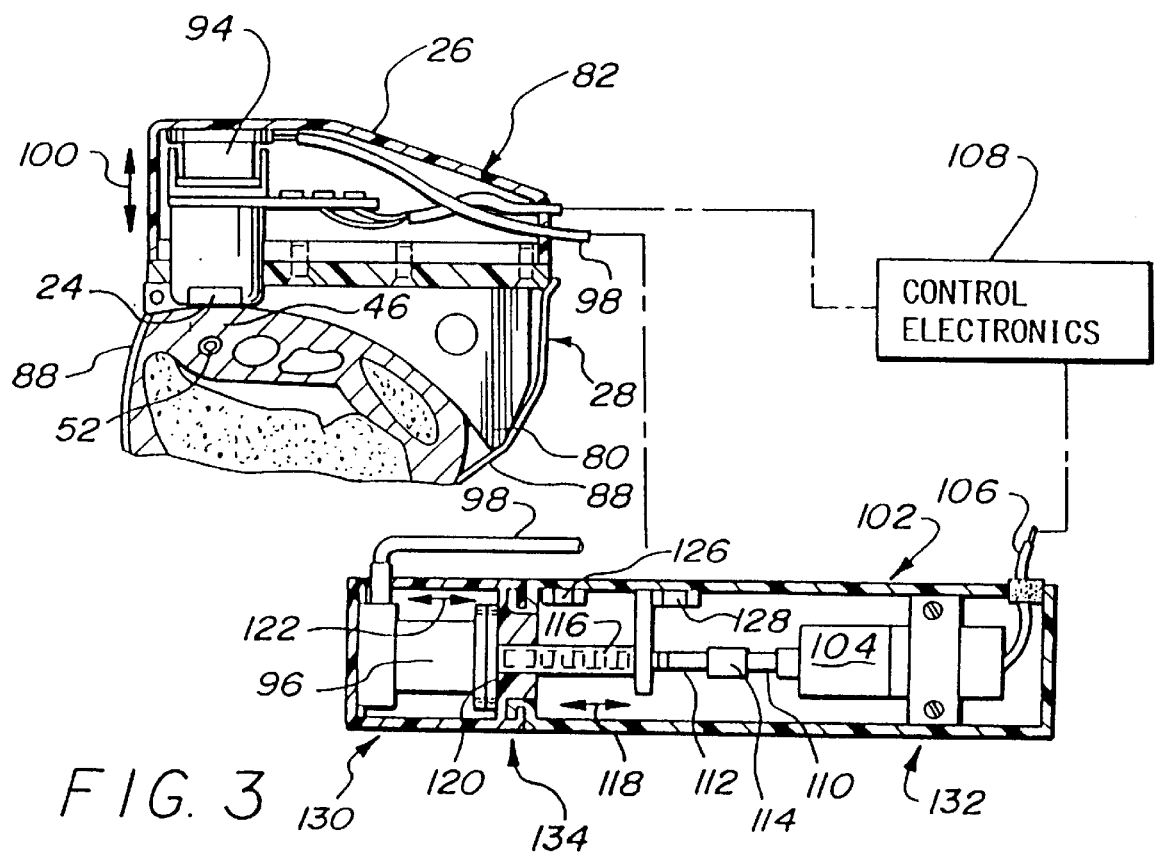
FIG. 3 is a diagrammatic schematic representation of a means for selectively positioning a sensor relative to an artery of interest.

Referring now to FIGS. 1 and 3 the details of one embodiment of an apparatus for mounting sensor 24 on a preselected portion of the patient's anatomy in order to place sensor 24 in communication with the tissue adjacent the preselected artery will be described. Wrist mount apparatus 28 generally comprises base portion 80 and transducer platform 82. Transducer platform 82 is attached to base portion 80 such that platform 82 can move laterally in the directions indicated at 84, and 86 pivotally. Base portion 80 includes restraining strap 88 for fixing base portion 80 to the wrist 22 of a patient. Base portion 80 includes first and second windows 90 and 92. When apparatus 28 is worn on the right wrist 22 of a patient, platform 82 is moved laterally in the direction shown at 84 to place tissue stress sensor 24 over window 90. Platform 82 is then pivoted downward toward wrist 22 to place stress sensor 24 in operative engagement (or communication) with tissue 46 overlying the radial artery. Similarly, when wrist mount apparatus 28 is placed on the left wrist of a patient (not shown), platform 82 is moved laterally over window 92 and pivotally 86 such that tissue stress sensor 24 is centered within second window 92. Therefore, wrist mount apparatus 28 is well suited to be used on the right or left wrist of a patient.

When it is desirable to use wrist mount apparatus 28 for placing tissue stress sensor 24 in operative engagement with the tissue surrounding the preselected artery, the following approach is preferably used. First, transducer platform 82 is moved laterally 84 such that first window 90 is generally unobstructed. Next, base portion 80 is placed on wrist 22 of the patient such that the first window 90 is generally centered upon the tissue overlying the artery of interest. Once this initial positioning has occurred, restraining strap 80 is placed around the wrist thereby securing base portion 80 to wrist area 22. Next, the artery of interest is palpated (generally by the medical professional using an index fingertip) to ensure that the artery of interest properly lies within the area framed by first window 90. If no arterial pulse can be detected with the current position, strap 88 is released and window 90 is moved to a new location where palpation is attempted once again.

Once window 90 is properly located over the preselected artery, platform 82 is moved laterally such that the tissue stress sensor 24 is generally above first window 90. Next platform 82 is pivoted 86 toward tissue 46 until platform 82 locks into its use position. Platform 82 is then positioned over the base portion 80 in the manner generally depicted in FIG. 3. In this position, wrist mount apparatus 28 is operative for use in the inventive system for non-invasively determining the arterial blood pressure of a patient.

Various features of wrist mount apparatus 28 including the more intricate details and features and advantages associated with the illustrated embodiment are explained in U.S. Pat. No. 5,271,405, issued on Dec. 21, 1993, and having common inventorship and assignee of interest with this application. The teachings of U.S. Pat. No. 5,271,405 are hereby incorporated by reference into this specification.

Apparatus for Properly Positioning the Sensor

FIG. 3 diagrammatically illustrates a cross-sectional view of one embodiment of a means for properly positioning sensor 24 relative to the tissue 46 adjacent the preselected artery. Sensor housing 26 is mounted to base 80. Fluid operated slave bellows 94 is mounted within sensor housing 26. Bellows 94 is attached to, at one of its ends, tissue contact stress transducer or sensor 24. As bellows 94 receives a displacement fluid from master bellows 96 via tubing 98, it expands downwardly 100, thereby causing tissue stress sensor 24 to engage tissue 46 overlying artery 52. Slave bellows 94 receives displacement fluid from master bellows 96 which is housed within displacement fluid source 102. Electric motor 104 is preferably a rotary motor, but it is recognized that other actuators such as linear electric motors can be used. Electric motor 104 is responsive to electrical signals received along cable 106, from control electronics 108, to rotate shaft 110. (Control electronics 108 is one portion of control electronics 30 referenced in FIG. 1.) Shaft 110 is coupled to lead screw 112 by way of shaft coupler 114. Lead screw 112 in turn threadedly engages translation nut 116 whereby the rotation of shaft 110 is translated into displacement 118 of translation nut 116. Displacement nut 116, in turn engages plate 120 of master bellows 96 whereby displacement 118 of translation nut 116 leads directly to the collapsing/expanding 122 of master bellows 96. Thus, it can be seen, that when slave bellows 94 is placed in fluid communication with master bellows 96 by way of tubing 98, any displacement 122 of master bellows 96 will result in the corresponding displacement of slave bellows 94. Accordingly, when electrical command signals are received via cable 106 the rotation by shaft 110 of lead screw 112 causes slave bellows 94 to be displaced as illustrated at 124.

Limit switches 126, 128 are placed in operative engagement with the movement of translation nut 116 that is threadedly engaged with lead screw 112 such that each respective limit switch 126, 128 is activated when translation nut 116 is at either extreme of its permissible travel. Limit switches 126, 128 are well known to those skilled in the art as general purpose electrical switches. Switches 126, 128 are also connected to a controller (not specifically shown) used to control the electrical signals delivered to motor 104, which, in turn, controls overall applanation processes. Preferably, the fluid used within the illustrated artery applanation actuator (sensor positioner) is hydraulic fluid in tubing 98, which is preferably Teflon tubing. It is to be understood, however, that other fluid mediums, such as compressed gas and the like may be used to displace slave bellows 94.

After motor 104 turns upper shaft 110 a predetermined number of revolutions, translation nut 116 travels along lead screw 112 such that master bellows 96 is at its maximum contraction, thereby placing slave bellows 94 at its maximum extension. When slave bellows 94 is at its maximum extension, tissue 46 overlying artery 52 is depressed thereby flattening artery 52.

Fluid displacement control source 102 is comprised of two sections, bellows section 130 and motor section 132. Sections 130 and 132 are coupled together via connector interface 134. Connector interface 134 can comprise any number of well known quick-disconnect type systems. The purpose of quick-disconnect 134 is to separate hydraulic circuit comprising tubing 98, slave bellows 94 and master bellows 96 from motor section 132. By providing a means whereby the hydraulic circuit may be separated from motor section 132, the integrity of the hydraulic circuit may be maintained should it ever need to be separated from the motor section 132 for the purpose of servicing or storing motor section 132. If no disconnect means 134 is provided to disconnect the motor drive section 132 from the bellows section 130, fluid displacement source 102 would have to be kept with wrist mount apparatus 28 at all times, unless, of course, tubing 98 is disconnected. Disconnecting hydraulic line 98 is generally considered undesirable because of the uncleanliness associated with leaking hydraulic fluid, the possibility of introducing contaminants into the hydraulic circuit and the difficulty associated with bleeding air from the hydraulic circuit when the applanation apparatus is used once more. Thus it can be seen that connector interface 134 is effective for joining bellows section 130 with motor section 132 during normal operating conditions of wrist mount apparatus and it is also effective for separating bellows section 130 from motor section 132 for storage or servicing, thereby maintaining the integrity of hydraulic circuits 98, 94 and 96.

The just described and illustrated means for positioning the sensor relative to the tissue surrounding the preselected artery is preferably used with the wrist mount apparatus illustrated in FIG. 1. It is to be understood that other mounting apparatus can be implemented with this invention depending upon the particular anatomy of the patient and the artery that is selected for monitoring purposes.

Figure 4A:
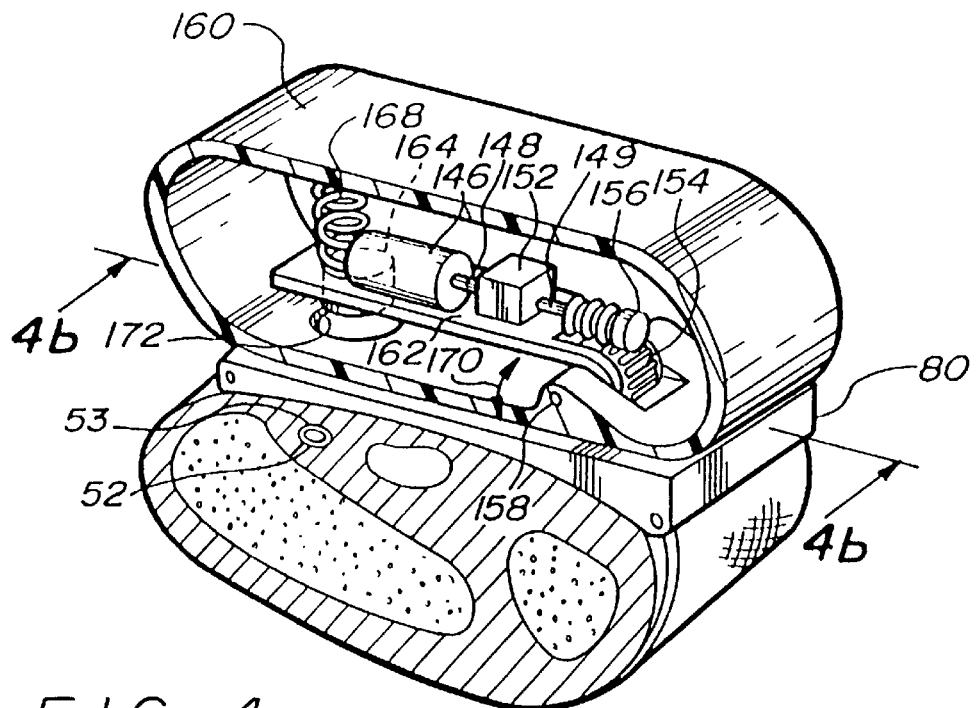
FIGS. 4a and 4b are diagrammatic schematic representations of a means for applanating an artery of interest using the sensor as generally depicted in FIG. 2.
Figure 4B:
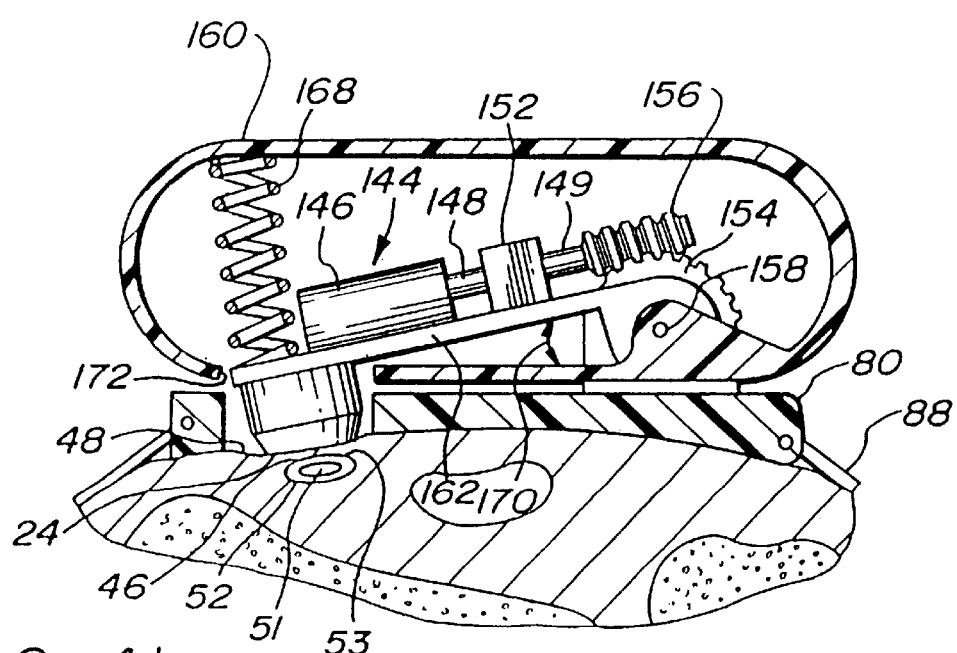

FIGS. 4a and 4b are cross sectional diagrammatic representations of another embodiment of a means for applanating the preselected artery. Base 80 is connected to the wrist of a patient via strap 88. Electric motor 144 is housed within sheath 160 and mounted on sensor mounting 162. Electric motor 144 includes motor housing 146 and motor shaft 148 which extends from motor housing 146 and is secured to sensor mounting 162. When motor 144 is made responsive to electrical signals, shaft 148 rotates, thereby causing sensor mounting 162 to rotate according to the arrows shown at 150. Motor shaft 148 is preferably fitted with gear reduction coupling 152. Gear reduction coupling 152 serves a two-fold purpose. First, gear 154 provides a reaction surface for worm gear 156 thereby enabling mounting 162 to pivot about pin 158. Second, gear 154 provides, in connection with worm gear 156, gear reduction means whereby the torque required to applanate artery 52 can be accomplished by choosing the correct capacity motor 144 in conjunction with the proper gear reduction ratio of gears 154 and 156.

Sheath 160 is pivotally mounted to motor shaft 148. Within sheath 160, arm 162 is fixed to shaft 148 and sensor assembly 164 is pivotally connected to arm 162 by way of pivot pin 158. Sensor assembly 164 engages sheath 160 by way of spring 168. Therefore, when motor shaft 148 is not applying a downward rotational torque 170 to arm 162, sensor 24 of sensor assembly 164 is retracted into sheath 160 and away from opening 172, thereby protected against inadvertent contact. Therefore, sheath 160 disposed about sensor mounting 162 protects sensor 24 within sensor assembly 164. When motor 144 rotates its output shaft 148, gear reduction means 152 is effective for translating the rotation of output shaft 148 into a rotation of shaft 149. Worm gear 156 is fixed to shaft 149 and accordingly translates the rotational motion of shaft 149 to reaction gear 154. Because reaction gear 154 is fixed to base 80, any rotational motion of worm gear 156 translates into rotating sensor mounting 162 about pin 158 (indicated at 170). This rotation of sensor mounting 162 causes sensor assembly 164 to pass through sheath opening 172 and engage sensor 24 to tissue 46 overlying artery 52. As this rotational motion is continued, the downward force of sensor assembly 164 on tissue 46 causes artery 52 to applanate. Once the rotational torque exerted by motor 144 onto output shaft 148 is extinguished, spring 168 is effective for returning sensor assembly 164 into sheath 160, thereby protecting sensor assembly 164 from inadvertent contact.

Further details regarding the embodiments of FIGS. 3, 4a and 4b and other embodiments of artery applanating means used in connection with this invention are explained in U.S. Pat. No. 5,240,007, issued on Aug. 31, 1993, having common inventorship and assignee of interest with this application. The teachings of U.S. Pat. No. 5,240,007 are hereby incorporated by reference into this specification.

Calibrating Means

Figure 5A:
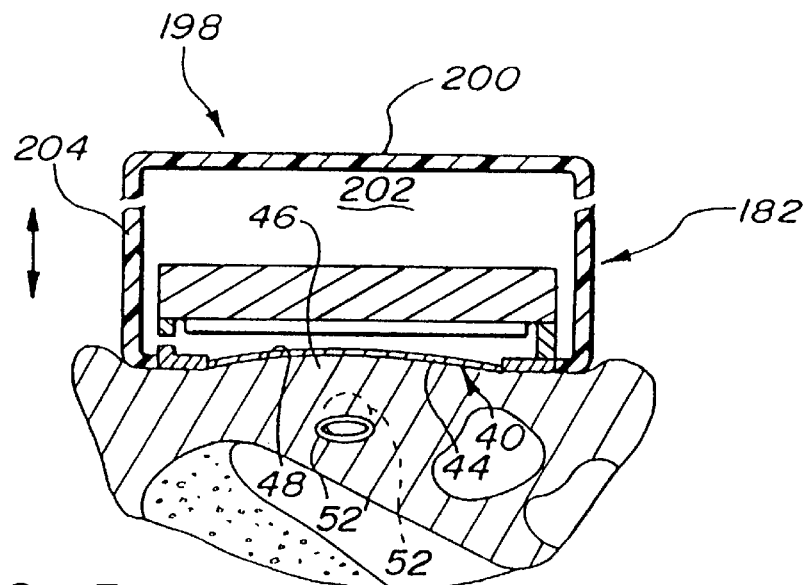
FIGS. 5a and 5b are a diagrammatic schematic representations of a means for calibrating a tonometry system designed in accordance with this invention.
Figure 5B:
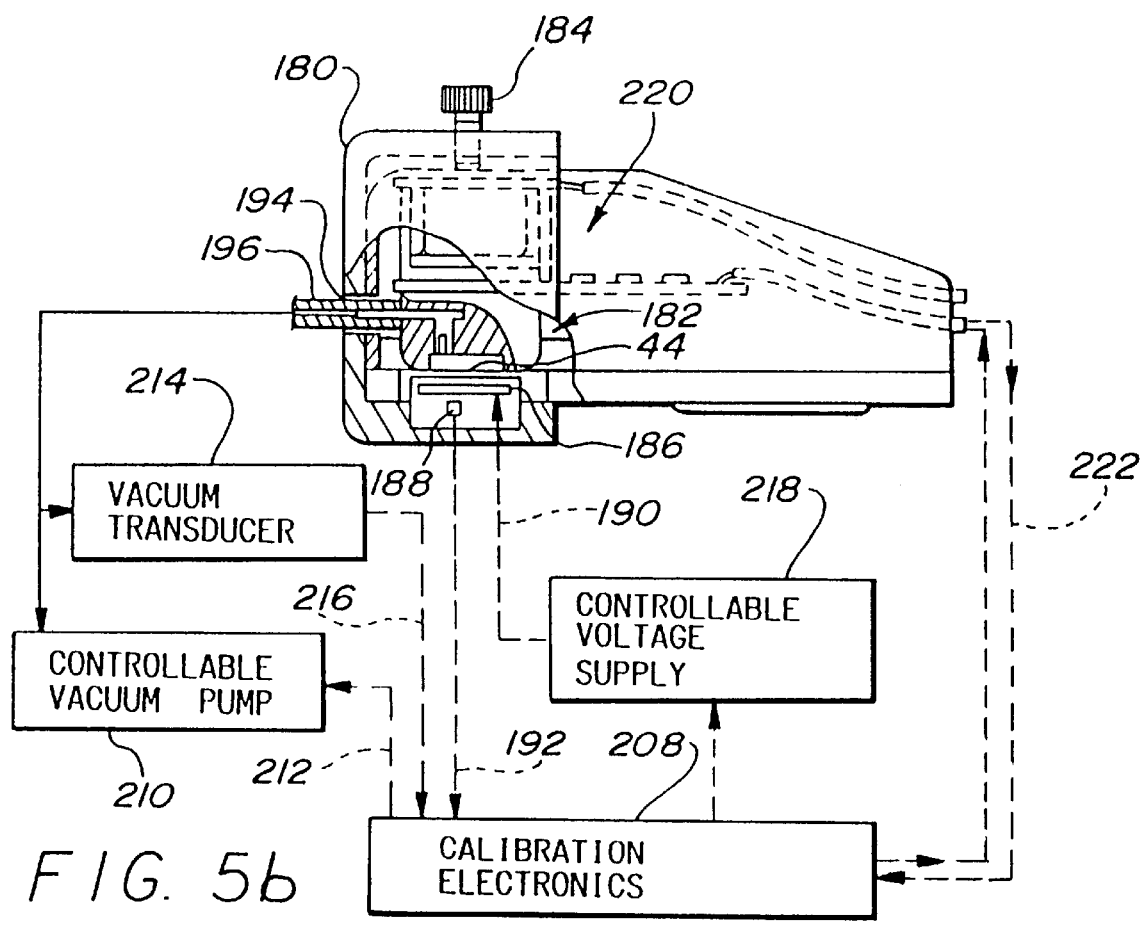

FIGS. 5a and 5b diagrammatically and, in block diagram form, illustrate one embodiment of a calibration means used in association with the tonometry system 20 of this invention. Calibration head 180 has a generally C-shaped structure that is adapted to engage sensory support structure 182. A portion of calibration head 180 includes fastening means for thumb screw 184, which is threadedly engaged to calibration head 180 and adapted to retain calibration head 180 to sensor support structure 182. Calibration head 180 also includes heater 186 and temperature sensor 188. Although heater 186 will be used throughout this specification to refer primarily to a device that adds thermal energy to diaphragm 40, heater 186 could also include a device capable of removing heat energy from diaphragm 40. Cooling diaphragm 40 may be desirable in some cases. Consequently, it is contemplated within this disclosure, that heater 186 includes any thermal device which can operate to heat or cool diaphragm 40. Heater 186 is preferably an electric-type heater that receives operating current through line 190. Temperature sensor 188 includes any type of thermal detecting device such as a thermocouple, thermistor, RDT, solid state sensor, or the like. The temperature sensed by sensor 188 is converted into an electric signal and sent to calibration electronics via line 192.

Calibration head 180 is provided with opening 194 to receive vacuum tube 196 thereby transmitting a source of vacuum into hermetically sealable chamber 198 (specifically shown in FIG. 5a) of sensor 24.

Responsive diaphragm 44 forms a part of continuous wall 200 of hermetically sealable chamber 198. Responsive diaphragm 44 is responsive to a differential pressure between the pressure within chamber 198 and the air pressure surrounding hermetically sealable chamber 198. Accordingly, it can be seen that diaphragm 44 of sensor 24 can be displaced by lowering the pressure within volume 202 and with respect to the air pressure outside of chamber 198 (air pressure outside of chamber 198 is typically atmospheric pressure, but this does not have to be the case). Thus, if a vacuum is placed on port 204 of chamber 198, diaphragm 44 will be displaced in the same manner it is displaced during actual use (when it is subjected to tissue stress). Accordingly, by applying a vacuum of known intensity to chamber 202, the fundamental relationship between deflection of diaphragm 44 and the pressure necessary to cause that deflection can be established.

It is important to note, that in this respect, the design of sensor 24 plays an important role in the calibration system of this invention. Specifically, designing hermetically sealable chamber 198 to make responsive diaphragm 44 a part of continuous wall 200, a calibrated vacuum can be used to effectively simulate the application of a calibrated pressure across responsive diaphragm 44 of sensor 24.

Heater 186 is mounted within C-shaped calibration head 180 such that it is in close proximity to, but does not directly contact, responsive diaphragm 44. In this manner, heater 286 is effective for heating diaphragm 44 but does not transmit any contaminants thereto, nor does it expose diaphragm 44 to damage potentially caused by bumping heater 186 against diaphragm 44. Preferably, heater 186 operates to uniformly heat the entire stress sensitive (or diaphragm) portion 44 of stress sensor 24. This uniform heating is preferably accomplished by extending heater 186 along the full length of diaphragm 40. Temperature sensor 188 is placed in close proximity to heater 186 for sensing the approximate temperature of diaphragm 40 and sending the sensed temperature along line 192 to calibration electronics 208. Vacuum tube 196 fluidly couples controllable vacuum pump 210 to inner chamber 198. Accordingly, a vacuum applied by pump 210 is effective for displacing diaphragm 40. Pump 210 is controlled by calibration electronics 208 via line 212. Voltage signals sent out from calibration electronics 208 to pump 210 control the amount of vacuum applied to diaphragm 44, thereby controlling its displacement. Vacuum transducer 214 senses the vacuum in tube 196 and transduces that vacuum into an electric signal that is transmitted to calibration electronics 208 via line 216.

The calibration means just described and illustrated in FIGS. 5a and 5b works basically as follows. Calibration electronics 208 first sends out a signal to the controllable voltage supply 210 to generally heat diaphragm 40 to a predetermined temperature. The predetermined temperature is preferably within the temperature range experienced by diaphragm 44 during actual operating conditions. Sensor 188 is responsive to the actual temperature of heater 186 and calibration electronics 208 constantly monitors and controls the diaphragm temperature and uses this temperature for generating corrective data for use in correcting the effects of tissue stress sensor temperature on the data generated by the sensor. After diaphragm 44 has stabilized at a predetermined temperature, various vacuum settings can be applied to diaphragm 44 thereby giving rise to various degrees of diaphragm deflection. Diaphragm deflection is sensed by sensing electronics (not particularly illustrated) and further conditioned by support electronics 220. Support electronics 220 encode the deflection of diaphragm 40 into electronic signals and transmit them to calibration electronics 208 along line 222. The calibration means just described is effective for measuring the displacement of diaphragm 44 in response to a known vacuum (which can be used to calculate the equivalent contact stress across diaphragm 44) at a known temperature. Thus, by setting various vacuum and temperature points and monitoring the electronic signals produced on line 222, a collection of characteristic data can be generated to generally define the calibration characteristics of diaphragm 40, sensor support electronics 220 and any other devices between calibration electronics and diaphragm 40.

The function of calibration electronics 208 is accomplished by using hardware or software techniques. If software techniques are utilized, a single system may be designed to function in a calibration mode and an operation mode. Thus, the same system (one portion of control electronics 30, for example) would be used for calibrating the sensor and monitoring its output during actual use conditions.

The calibration means and preferred methodology for calibrating tonometry system 20 have just been described. Further details and more intricate substeps within the methodology are explained in U.S. Pat. No. 5,195,522, issued on Mar. 23, 1993, having common inventorship and assignee of interest with this application. The teachings of U.S. Pat. No. 5,195,522 are hereby incorporated by reference into this specification.

Tonometry Methodology

Figure 6:
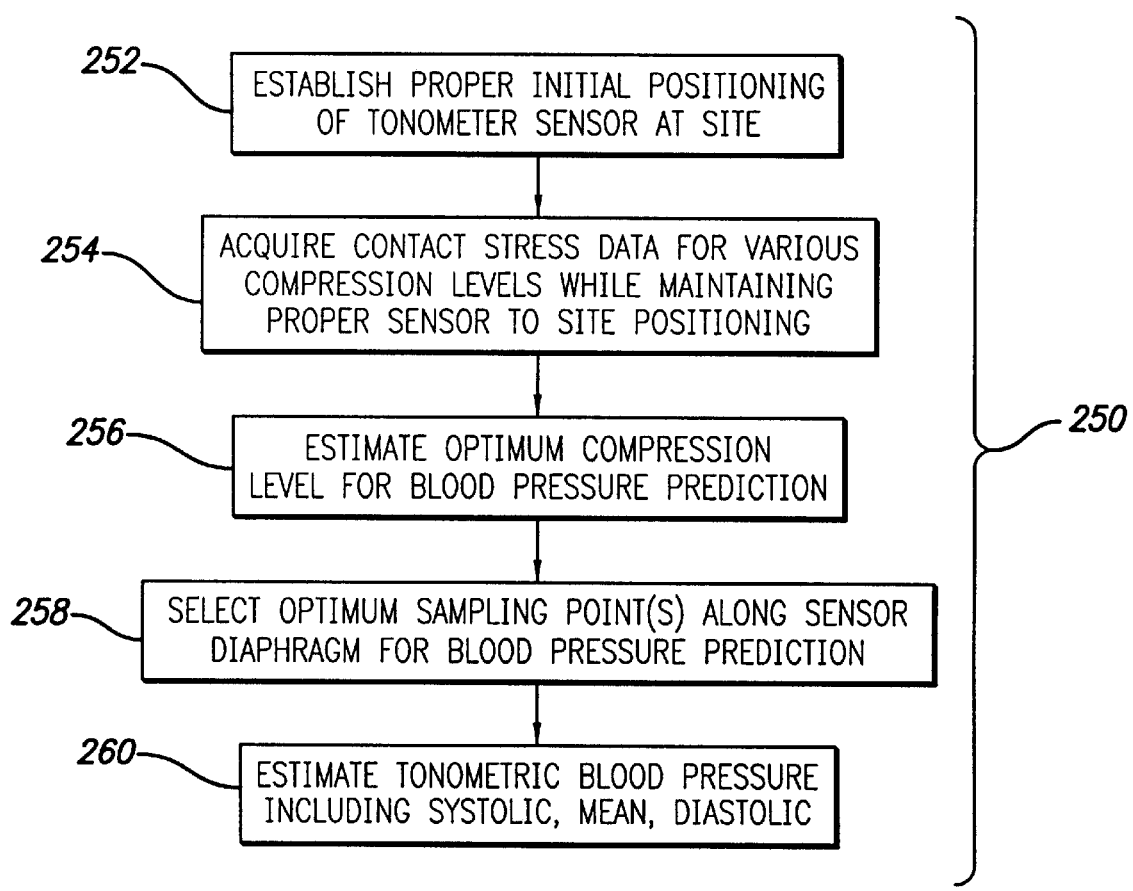
FIG. 6 is a flow chart diagram illustrating the basic steps taken in executing the methodology associated with this invention.

FIG. 6 illustrates, in flow diagram form, the basic methodology 250 associated with this invention. FIG. 6 shows that continuous tonometric measurement of blood pressure can be achieved according to five basic steps. First 252, establish proper initial positioning of the tonometer sensor at the site on the patient's anatomy where the preselected artery of interest is located. Second 254, acquire contact stress data for various compression levels, using the stress sensor, while maintaining proper sensor positioning relative to the patient's anatomy. Third 256, estimate an optimum compression level for blood pressure prediction. Fourth 258, select an optimum sampling region(s) along the sensor diaphragm for use in actual blood pressure calculation and prediction. Fifth 260, estimate tonometric blood pressure including systolic, mean and diastolic pressure values. Each of the basic steps outlined in FIG. 6 include a number of substeps and specific methodologies. These substeps and the details of the methodology will be discussed in further detail below.

Figure 7:
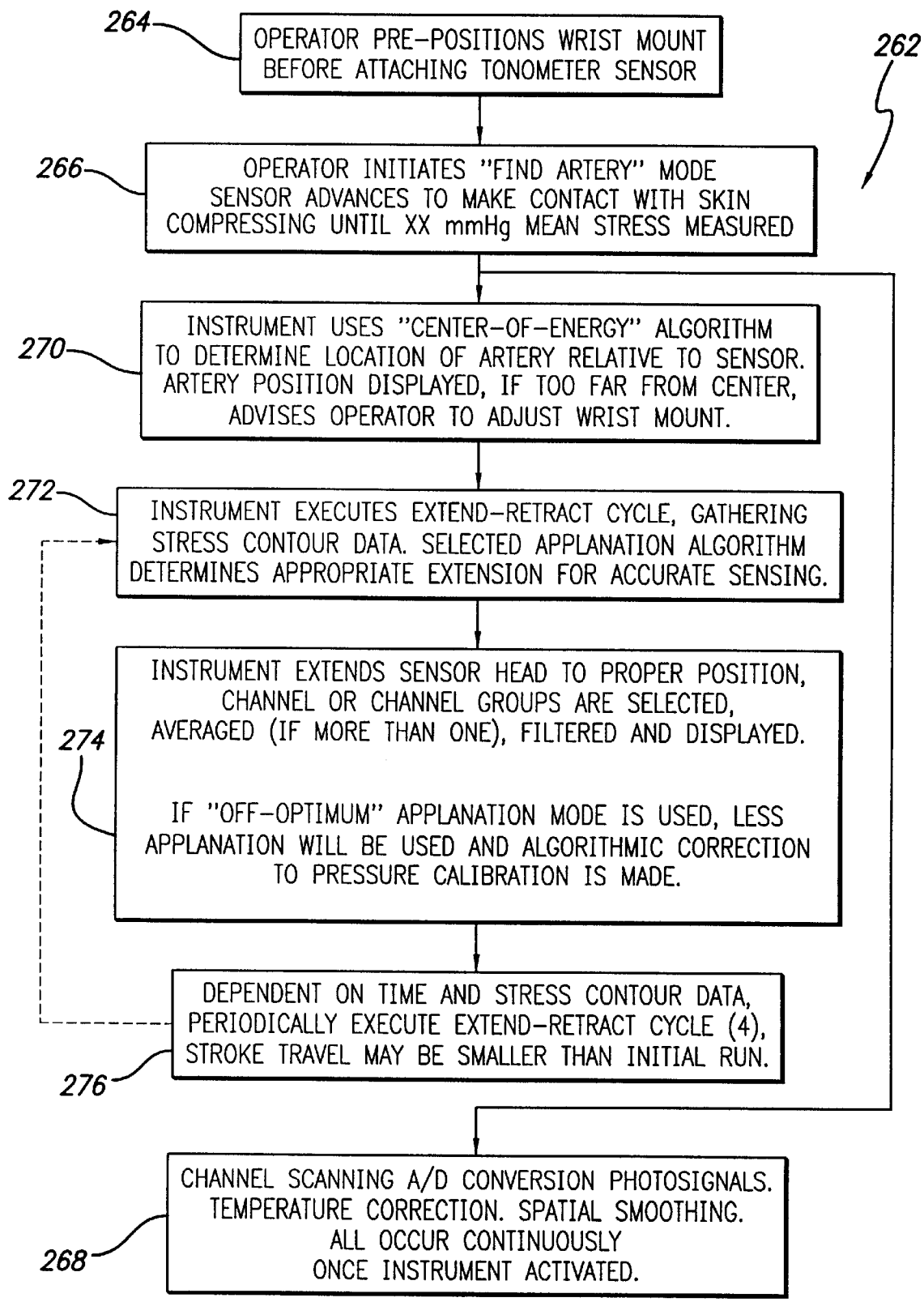
FIG. 7 is a flow chart diagram representation of a preferred methodology associated with this invention.

FIG. 7 illustrates, in flow diagram form, a presently preferred method 262 of continuously monitoring a patient's blood pressure used in association with this invention. First 264, the operator or medical professional pre-positions a mounting apparatus on the patient's anatomy in the vicinity of the preselected artery of interest. Next 266, the operator attaches the tonometer sensor and initiates "the find artery" mode. In the find artery mode, the sensor advances to make contact with the skin and tissue adjacent the preselected artery and compresses that tissue until a preselected mean stress is measured; typically in units of millimeters of mercury. In the most preferred embodiment, several functions 268 occur on a continuous basis once the sensor instrument is activated, including channel scanning, analog to digital conversion of photosignals, temperature correction and spatial smoothing.

Next 270, the instrument or sensor uses the "center-of-energy" algorithm to determine the location of the preselected artery relative to the sensor. The artery position is preferably concomitantly displayed (for example, on display device 32) and if the artery is determined to be too far from the center of the sensor diaphragm 44 the output display device 32 preferably advises the operator to adjust the mounting apparatus. Next 272, the tonometer executes the "extend-retract cycle," to thereby gather stress contour data. The appropriate extension position for the sensor relative to the housing is determined depending upon the applanation algorithm that is selected in order to achieve accurate sensing given the conditions under which the blood pressure is to be monitored.

Under some circumstances, it will be desirable to have multiple monitoring positions. For example, one displacement may yield optimal diastolic estimation while a second will yield optimal systolic estimation.

Next 274, the instrument (via the control electronics and moving means detailed previously) extends the sensor head to the proper monitoring position(s), the region or channel groups along the diaphragm are selected and averaged (in the case when more than one channel is selected). Then the selected region produces signals corresponding to stress contour data in the tissue and those signals are filtered and preferably displayed in a user-friendly format. It is important to note that if an "off optimum" applanation mode is used, less applanation is implemented and an algorithmic correction to the pressure calibration is made at this stage. The instrument preferably executes a modified extend/retract cycle 276 on a periodic basis which is dependent on the time and stress contour data that is achieved in step 272, for example. It is important to note that during the periodic reexecution of the extend/retract cycle that the stroke travel or the movement of the sensor in a direction toward the preselected artery may be smaller than initially required when initiating a blood pressure monitoring operation.

As was described in conjunction with FIGS. 1, 3, 4*a* and 4*b*, the tonometric technique for monitoring blood pressure associated with this invention involves positioning the transducer or sensor over a preselected artery and then pressing the sensor against tissue overlying the artery so as to flatten (or applanate) artery 52. The transducer preferably includes stress sensitive element. One or more continuous stress sensitive diaphragm that is capable of sensing stress throughout its length is most preferred. The stress sensitive element is designed such that it is able to detect (and distinguish between) stresses created along its length. The portion(s) of the stress sensitive element that is preferably selected for monitoring blood pressure is that portion centered over the artery because that portion typically provides an accurate measure of arterial blood pressure. The portions of the stress sensitive element that do not directly overly the artery do not provide as accurate a measurement of arterial blood pressure as that from the centered portion.

Other factors also influence the accuracy of arterial blood pressure measurement. One primary factor influencing accuracy is the degree, or extent, to which the artery of interest is applanated at the time the stress sensitive element is measuring tissue stress. Although fairly accurate blood pressure measurements may be made over a wide range of applanation states, it is generally accepted that there exists a substantially unique applanation state that produces the most accurate determination of arterial blood pressure. This unique applanation state is commonly known as the optimum applanation state. Prior methods for applanating include an attempt to relate optimum artery applanation to a hold down pressure where hold down pressure is defined as the pressure applied against the pressure transducer as the transducer is forced against the tissue adjacent the artery of interest.

It is Applicants' theory that the techniques taught by the prior art are improperly focused and accordingly may not produce results as accurate as the methodologies disclosed herein and used in connection with this invention. Specifically, while hold down pressure is a parameter that may loosely correlate to the artery applanation state, it is believed that there are a number of more useful parameters. The methodologies used in association with this invention set forth a number of applanation state parameters (ASP) which are believed to provide a superior measure (or indication) of applanation state. This belief is founded on the fact that the methodologies used in association with this invention for determining optimum arterial applanation are based upon tonometric parameters which are sensitive to the physical events that take place when an artery is applanated.

When the stress sensitive element 44 of sensor 24 is not in contact with top surface 48 of tissue 46, opening (or lumen) 51 of artery 52 maintains a generally circular cross section. When the stress sensitive element is brought in contact with and bears against surface 48 of tissue 46, different degrees of artery distortion occur, depending, in part, upon the displacement caused by stress sensitive element 40 against surface 48. As can be appreciated from the drawings (i.e., FIG. 4*b*), when the amount of downward displacement of the sensor (i.e., toward the artery), lumen 51 of artery 52 is generally elliptical. As displacement increases beyond that shown in FIG. 4*b*, for example, the top surface of artery 52 assumes a generally planar orientation. At this applanation state, localized contact stresses at the tissue surface (over the vessel center) are balanced with the stresses caused by the arterial blood pressure. When the top surface 53 of artery 52 is generally planar, artery 52 is said to be in an optimally applanated state. If displacement of the sensor is increased beyond that causing a generally planar top surface of artery 52, a condition of buckling (or collapsing) occurs in a very small localized region of the vessel wall. In this buckled state, region 50 is incapable of carrying significant additional localized contact stress. Accordingly, if displacement is increased from that which causes a generally planar top of the artery to that which causes buckling, the additional contact stresses created along the buckled portion are shed (or transferred) to adjacent (not yet buckled) regions of the artery wall. By shedding stress from one buckled region to adjacent non-buckled regions (thereby causing the previously unbuckled regions to then buckle) the stress contour exhibits a non-linear behavior. Many of the methodologies used in association with this invention take advantage of this non-linear phenomenon to predict optimum applanation state.

Monitoring arterial blood pressure begins by establishing the proper initial positioning of the stress sensor on the patient's anatomy adjacent the site of the preselected artery. Once proper initial positioning is established, stress sensor 24 collects contact stress data 254. Once the stress data has been collected, applanation means 94, 96 (see FIG. 4) moves sensor 24 thereby establishing a new compression level. This process of collecting stress data continues for each unique applanation state. The movement of applanation means 94, 96 is preferably accomplished in a step-wise fashion or in a continuously varying fashion. Once applanation means 94, 96 has completed its applanation cycle, systolic, diastolic, pulsatile, and waveform mean contact stresses are derived as functions of position along the stress sensitive element and also as functions of applanation state. From the acquired contact stress data, one or more optimum applanation methodologies are utilized for determining the optimum applanation compression level for arterial blood pressure estimation. Once the optimum arterial compression level is determined, certain portions of the data collected during the optimum applanation level are selected for blood pressure estimation. Those selected sample points of contact stress data are then used for estimating the arterial blood pressure.

When implementing methodologies for non-invasively determining arterial blood pressure, it is helpful and convenient to develop various classifications of functions. Two particular classes of parameters (or functions) disclosed herein are applanation optimization parameters and applanation state parameters. Applanation optimization parameters (AOP) are parameters that provide guidance in selecting the optimum amount of artery applanation. The applanation state parameters (ASP) are parameters that indicate the degree to which the artery has been flattened or distorted as it is acted upon by tissue stress sensor 24. To generalize the relationship between the AOP and the ASP, the AOP is a function of the applanation state parameter, i.e.: AOP=f(asp) or, in shorthand, AOP(ASP). One or more functions AOP(ASP) are preferably used for determining the "best" or optimum artery applanation state. Each method used in association with this invention generally operates by adjusting a selected ASP until a preferred or optimum AOP(ASP) is found. For example, in one method when AOP(ASP) equals 1.00, preferred conditions exist for estimating arterial blood pressure based upon collected contact stress data.

An example of an applanation state parameter would be simply monitoring the displacement that is applied against the stress sensor as it is displaced against the tissue overlying the artery of interest. For example, a displacement of 10 mils (i.e.: 0.010 inch) may receive an applanation state parameter of 1; 20 mils equals an ASP value of 2, etc. Another method of deriving applanation state parameters is simply to measure the force against tissue stress sensor 24 as it is displaced into tissue 24 by moving means or bellows 94, 96.

Still another applanation state parameter may be derived by calculating the average contact stress across the entire length of the stress sensitive element. This method may include applanating an artery to a first state and then, while held in that state, calculating the average contact stress across the entire length of the stress sensitive element. Mathematically, this method is expressed as follows:

$$AASI_1 = \sigma avg(AAS_1) = \frac{\int_o^L \sigma(x) AASI \cdot dx}{\int_o^L dx}$$

where:

$\sigma_{avg}(AAS_1)$=average stress value across the length of the stress sensitive element while the preselected artery undergoes the first artery applanation state;

$AAS_1$=first artery applanation state;

$AASI_1$=first artery applanation state index;

$\sigma(x)AAS_1$=stress data sensed by the stress sensitive element at location x while the artery of interest undergoes the first artery applanation state;

x=equals the location along the length of the stress sensitive element; and

O and L equal the limits of integration across the length of the stress sensitive element.

Further details regarding applanation state parameters, applanation optimization parameters and intricate details regarding 12 separate methods that can be used in association with this invention are explained in U.S. Pat. No. 5,273,046, issued Dec. 28, 1993, having common inventorship and assignee of interest with this application. The teachings of U.S. Pat. No. 5,273,046 are hereby incorporated by reference into this specification.

The methods that are preferably used for accomplishing optimum applanation in association with this invention can be generically described as follows. First, the stress sensitive element of the tissue stress sensor is placed in communication with tissue that is adjacent the preselected artery. Second, the stress sensitive element is oriented such that the length of the continuous diaphragm expands beyond the lumen of the preselected artery. Third, the stress sensitive element is used to varyingly compress the preselected artery, to thereby applanate the artery through a plurality of stages. At each of the applanation stages just mentioned, at least one electrical signal obtained from the tissue stress sensor represents stress data across the length of the stress sensitive element. That stress data includes a plurality of stress datum where each stress datum represents stress communicated to a predetermined portion of the stress sensitive element from the tissue adjacent the preselected artery, and each predetermined portion of the stress sensitive element lying along the length of that element.

For each applanation stage, the stress data, just generally described, is used for selecting and computing an applanation optimization parameter. The applanation optimization parameter is preferably selected from a group of parameters comprising a pulse parameter, distribution breadth parameter, pulse spread parameter, spatially averaged stress parameter, stress spatial curvature parameter and a stress variation parameter, Next, an applanation state parameter is selected and computed. Then the selected applanation optimization parameter is related to the applanation state parameter. Then a value associated with a characteristic feature of the selected applanation optimization parameter is determined relative to the artery applanation state parameter wherein the characteristic feature is indicative of the optimum arterial compression. At this point, the optimum arterial compression is estimated to be that degree of artery applanation that produces the applanation optimization parameter value determined (in the previous sentence).

Although operating at the optimum applanation state directly produces the most accurate indication of arterial blood pressure, prolonged positioning of the tonometric sensor at that state is known to produce a varying degree of patient discomfort. This is primarily due to the tissue displacement associated with achieving and maintaining optimum arterial applanation. Thus, it is desirable to find a nonoptimum or off-optimum applanation state which is comfortable to the patient and which does not cause tissue damage even in the cases where the artery is maintained in the off-optimum applanation mode for extended periods of time. Ideally, such a state of operation will yield arterial blood pressure measurements that meet acceptable accuracy standards.

Accordingly, it is within the scope of this invention to provide a method for operating tonometry system 20 at an off-optimum applanation mode to address the concerns mentioned above. The preferred methodology for operating tonometry system 20 in an off-optimum applanation mode is disclosed in U.S. Pat. No. 5,261,412, issued on Nov. 16, 1993, and having common inventorship and assignee of interest with this application. The teachings of U.S. Pat. No. 5,261,412 are hereby incorporated by reference into this specification.

Generally speaking, operating the tonometry system of this invention at an off-optimum arterial applanation state is described as follows. The sensor 24 is placed in communication with the tissue adjacent the preselected artery and applanate the preselected artery through a plurality of applanation states. At each of those applanation states at least one electrical signal is obtained from sensor 24 in the same manner described for optimum applanation described above. An optimum arterial applanation state is determined. Then an error value associated with the off-optimum arterial applanation state is computed (the off-optimum arterial applanation state is different from the optimum arterial applanation state just determined).

The preselected artery is then applanated to the off-optimum arterial applanation state. While the artery is applanated at the off-optimum applanation state, tissue stress data is obtained from the tissue stress sensor 24. The data obtained from the sensor during the off-optimum applanation state is combined with the error value that is computed as being associated with that off-optimum arterial applanation state to yield corrected stress data that approximates stress data associated with the tissue adjacent the preselected artery such that the stress data is interpreted as if the artery were applanated at the optimum arterial applanation state.

Determining which Portion or the Sensor is Best Located for Detecting Arterial Blood Pressure The nature of the continuous flexible diaphragm used in sensor 24 requires that only a selected portion of the stress sensitive element or diaphragm be used for interpreting the stress communicated to the sensor from the tissue adjacent the preselected artery in order to determine and monitor arterial blood pressure. As diaphragm portion 44 responds to tissue stress, the electromagnetic radiation reflected from the active area of diaphragm 40 is dispersed. This action reduces the amount of radiation that would otherwise reach the neighboring receivers 62 and causes a reduction in their output signal. This dispersion of electromagnetic radiation rays 61 away from selected receivers produces only a small deviation in the output signal of the select receivers (hereinafter referred to as the sensor's inherent small signal current to total current ratio or small Isc/Itc ratio), and accordingly it is important to choose the geometric relationship of diode 60, receiver 62 and responsive portion 44 of wafer 40 to optimize the change of optical power received as a function of diaphragm displacement.

The detailed relationship between the methodology for determining the portion of sensor diaphragm 40 that is best located for estimating arterial blood pressure and the preferred configuration and design of sensor 24 are explained in U.S. Pat. No. 5,263,484, issued on Nov. 23, 1993, and having common inventorship and assignee of interest with this application. The teachings of U.S. Pat. No. 5,263,484 are hereby incorporated by reference into this specification.

One preferred method for determining the monitoring portion of the sensor diaphragm (that portion used for determining arterial blood pressure) is referred to by Applicants as the "contact stress energy method". The contact stress energy method is based upon the theory that the energy coupling between the preselected artery and the contact stress sensitive element is the greatest in the immediate vicinity of the artery. Thus, one can determine the portion of the stress sensitive element that directly overlies the preselected artery by determining the portion of the stress sensitive element that is in receipt of the maximum contact stress energy. In the same procedures, the "find artery" mode is completed by locating the artery relative to the sensor diaphragm.

The contact stress energy method uses the square of the contact stress values to obtain a measure of contact stress energy and thereby construct a relationship between contact stress energy and position along the length of the stress sensitive element. The centroid of the contact stress energy contour is calculated, thereby yielding a location along the stress sensitive element that is used for determining arterial blood pressure. In mathematical terms, the centroid of contract stress energy is calculated as follows:

$$\overline{X} = \left( \int_b^c x \cdot E(x) \cdot dx \right) \bigg/ \left( \int_b^c E(x) \cdot dx \right) \qquad (1)$$

where:

$\overline{X}$=centroid of energy;

x=location along the length of the stress sensitive element;

E(x)=stress energy at location x; and b,c=the limits of integration.

Wherein, contact stress energy E(x) is computed as follows:

$$E(x) = (\sigma(x))^2 \qquad (2)$$

where:

E(x)=stress energy at location x; and

σ(x)=stress datum sensed by stress sensitive element at location x.

Figure 8:
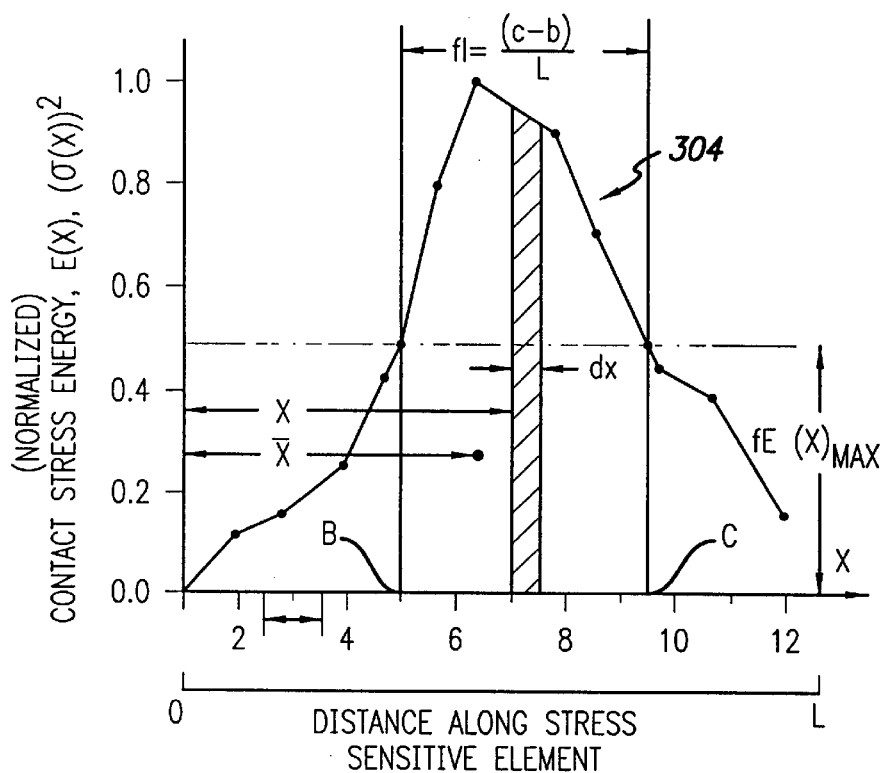
FIG. 8 is a graphical representation of a normalized contact stress energy curve plotted as a function of distance along a stress sensitive element.
Figure 9:
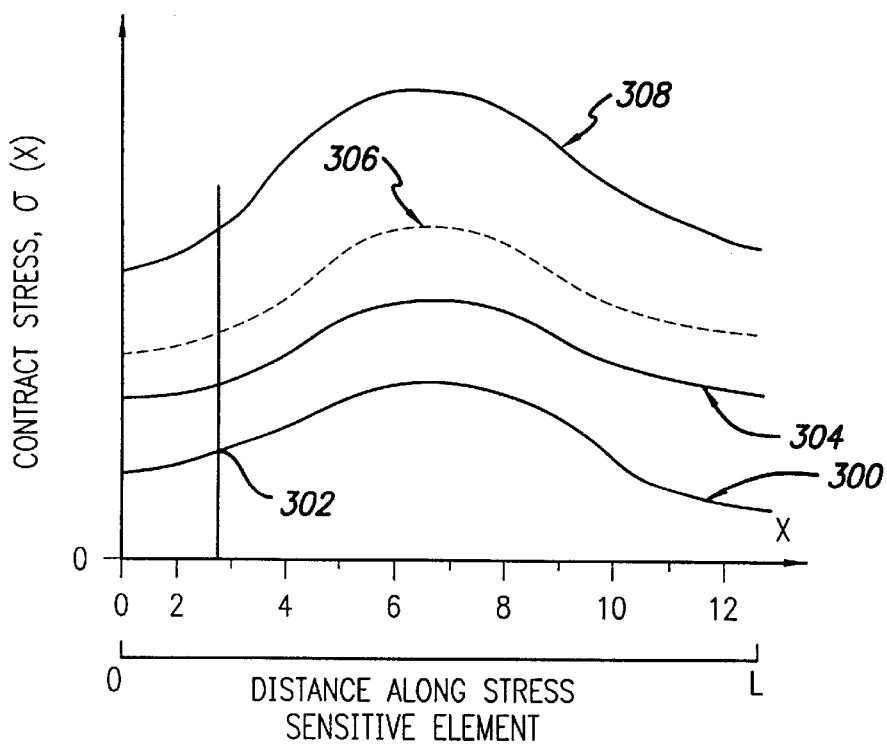
FIG. 9 is a graphical representation of contact stress versus distance along the length of a stress sensitive element.

The above referenced methodology is demonstrated graphically in FIG. 8. To implement the contact stress energy method, one must first select one of the stress contours as set out in FIG. 9. While anyone of the four stress contours may perform satisfactorily when implementing the contact stress energy method, the pulsatile stress energy contour is presently preferred. Thus, after obtaining pulsatile stress values across the length of the stress sensitive element (for example, as depicted in graph 300 of FIG. 9), each pulsatile stress value (exemplified at 302) is squared, thereby relating contact stress energy E(x) to the distance along the stress sensitive element. The centroid of the contact stress energy curve 302 is found by applying formula (1) as set out above.

The contact stress energy method of determining which portion of a stress sensitive element is best suited for determining arterial blood pressure uses a centroid of energy approach. Further details regarding the centroid of energy approach and the preferred methodology associated with that approach are explained in U.S. Pat. No. 5,263,484.

The preceding description shows that tonometry system 20 designed in accordance with this invention provides the ability for continuously monitoring arterial blood pressure in a noninvasive manner. Selected components and methodologies associated with tonometry system 20 have been fully described in this specification. Further details and embodiments that can be used in association with tonometry system 20 are found in the various United States patent applications that are incorporated by reference into this specification.

The preceding description is exemplary rather than limiting in nature. Variations and modifications are possible without departing from the spirit and purview of this invention. The scope of this invention is to be limited only by the appended claims.

What is claimed is:

1. A system for continuously monitoring a patient's arterial blood pressure, comprising:
    a sensor having a continuous stress sensitive diaphragm that is adapted to be deformed responsive to stress within tissue adjacent a preselected artery of the patient, the sensor having a radiation source separate from the continuous diaphragm, the source irradiating the diaphragm with electromagnetic radiation, and also having an electromagnetic radiation receiver mounted adjacent and separated from the diaphragm such that the receiver receives electromagnetic radiation reflected from the diaphragm, the sensor sensing deformations from selected portions along said diaphragm from the reflected electromagnetic radiation and produces a vessel stress signal representing the deformation along each selected portion of said diaphragm;
    a mounting apparatus for placing said sensor in a relatively fixed location relative to a preselected portion of the patient's anatomy associated with the preselected artery, the mounting apparatus including:
        a base portion configured to be mounted on said preselected portion of the patient's anatomy,
        a sensor platform movably engaged to the base portion, the sensor platform including a sensor housing, and
        a quick disconnector connecting said sensor platform to said base portion, whereby said disconnector allows said sensor platform and said sensor to be quickly removed from said base portion; and
    means for adjustably moving said sensor relative to the tissue adjacent the artery of interest, whereby said sensor is placed inoperative engagement with the tissue adjacent the preselected artery for determining the blood pressure within the preselected artery.

2. The system of claim 1, wherein said mounting apparatus is adapted to be placed on a wrist of a patient.

3. The system of claim 1, wherein said moving means moves said sensor to bear against the tissue adjacent the preselected artery such that said sensor applanates the preselected artery.

4. The system of claim 3, wherein said moving means comprises a reservoir of displacement fluid; and
    a bellows in fluid communication with said reservoir mounted between said mounting apparatus and the sensor and adapted to respond to a pressure of said fluid in said reservoir and to displace said sensor into operative engagement with the tissue adjacent the preselected artery, thereby applanating said artery in response to a displacement of said fluid.

5. The system of claim 3, wherein said moving means comprises a sensor head portion for housing said sensor;
    and a motor having a pivoting output shaft, said motor being attached between said mounting apparatus and said sensor head portion for pivoting said sensor head portion thereby causing said sensor to be pivotally moved into operative engagement against the tissue adjacent the preselected artery whereby the preselected artery is applanated by said sensor.

6. The system of claim 1, further comprising control electronics coupled with said sensor for performing at least one function from a set of control functions, said set of control functions comprising:
    determining a location of the preselected artery relative to said continuous diaphragm along a length of said diaphragm;
    determining an optimum applanation state of the preselected artery, wherein said optimum applanation state is defined by one or more members of a set of applanation parameters and said optimum applanation state is that state of applanation best suited for blood pressure determination;
    determining a desired location of said sensor relative to said mounting apparatus such that a desired applanation state is achieved in the preselected artery;
    storing a set of stress data that is collected by said sensor, said stress data being indicative os stress communicated to said sensor from the tissue adjacent the preselected artery, wherein said stress is caused by arterial pulsations;
    processing said stress signal to thereby produce a waveform signal corresponding to a waveform that is descriptive of the arterial blood pressure within the preselected artery; and
    processing said stress signal to thereby determine a systolic blood pressure within the preselected artery, a diastolic blood pressure within the preselected artery and a mean blood pressure within the preselected artery, respectively.

7. The system of claim 6, wherein said system is adapted to operate when the preselected artery is maintained in an off-optimum applanation state that is different from said optimum applanation state and wherein said control electronics generate correction data that is used to produce a corrected said stress signal when said stress signal corresponds to tissue stress caused while the preselected artery is in said off-optimum applanation stat such that said corrected stress signal corresponds to a stress signal produced while the preselected artery is in said optimum applanation state.

8. The system of claim 1, further comprising means control electronics adapted to receive said vessel stress signal from said sensor and capable processing said vessel stress signal to produce an output indicative of the arterial blood pressure of the preselected artery.

9. The system of claim 1, further comprising a calibration head disposed in close proximity to said diaphragm and a heater attached to said calibration head for altering a temperature of said diaphragm.

10. The system of claim 1, further comprising:

a heater for selectively altering a temperature of said diaphragm;

a source of reduced air pressure operative coupled to the sensor for displacing said diaphragm; and control electronics coupled with said sensor and configured to receive stress signals representing the displacement of the diaphragm in response to said altering of said temperature, the control electronics being configured to analyze the stress signals and to correct the effects of the temperature on said stress signal produced by said sensor.

* * * * *

UNITED STATES PATENT AND TRADEMARK OFFICE
CERTIFICATE OF CORRECTION

PATENT NO. : 6,290,650 B1
DATED : September 18, 2001
INVENTOR(S) : Robert D. Butterfield et al.

It is certified that error appears in the above-identified patent and that said Letters Patent is hereby corrected as shown below:

<u>Column 14,</u>
Lines 15-20, in the divisor of the equation, change " $\int_0$ ", to read -- $\int_0^L$ --.

Signed and Sealed this

Twelfth Day of March, 2002

Attest:

*Attesting Officer*

JAMES E. ROGAN
*Director of the United States Patent and Trademark Office*